(12) United States Patent
Thome

(10) Patent No.: US 12,042,263 B2
(45) Date of Patent: Jul. 23, 2024

(54) MAGNETIC FIELD DISTORTION DETECTION AND CORRECTION IN A MAGNETIC LOCALIZATION SYSTEM

(71) Applicant: St. Jude Medical, Cardiology Division, Inc., St. Paul, MN (US)

(72) Inventor: Alexander P. Thome, St. Paul, MN (US)

(73) Assignee: ST. JUDE MEDICAL, CARDIOLOGY DIVISION, INC., St. Paul, MN (US)

(*) Notice: Subject to any disclaimer, the term of this patent is extended or adjusted under 35 U.S.C. 154(b) by 353 days.

(21) Appl. No.: 17/604,297

(22) PCT Filed: Apr. 16, 2020

(86) PCT No.: PCT/IB2020/053632
§ 371 (c)(1),
(2) Date: Oct. 15, 2021

(87) PCT Pub. No.: WO2020/212916
PCT Pub. Date: Oct. 22, 2020

(65) Prior Publication Data
US 2022/0211292 A1 Jul. 7, 2022

Related U.S. Application Data

(60) Provisional application No. 62/836,435, filed on Apr. 19, 2019.

(51) Int. Cl.
*A61B 5/06* (2006.01)
*A61B 5/00* (2006.01)
(Continued)

(52) U.S. Cl.
CPC ............ *A61B 5/062* (2013.01); *A61B 5/6852* (2013.01); *G01R 33/285* (2013.01); *G01R 33/56* (2013.01)

(58) Field of Classification Search
CPC .... A61B 5/062; A61B 5/6852; G01R 33/285; G01R 33/56
See application file for complete search history.

(56) References Cited

U.S. PATENT DOCUMENTS 6,233,476 B1 5/2001 Strommer et al.
6,498,944 B1 12/2002 Ben-Haim et al.
(Continued)

FOREIGN PATENT DOCUMENTS

WO 2014141113 A2 9/2014
WO 2017130135 A1 8/2017

*Primary Examiner* — Dixomara Vargas
(74) *Attorney, Agent, or Firm* — Billion & Armitage

(57) ABSTRACT

Aspects of the present disclosure are directed to systems and apparatuses for detecting and correcting for magnetic field distortions within a magnetic field used for medical magnetic localization systems. In one example embodiment, a system is disclosed including a magnetic field generator and a magnetic detection sensor. The magnetic field generator generates the magnetic field for localization of a catheter within the patient. The magnetic detection sensor includes a plurality of sensor coils positioned at fixed distances and orientations relative to one another. Each of the sensor coils sense the magnetic field within a sensing region aligned with a longitudinal axis of the sensor coil, and outputs an electrical signal indicative of the sensed magnetic field. The plurality of sensing coils form two substantially contiguous sensing regions, a first continuous sensing region above the magnetic detection sensor, and a second continuous sensing region below the magnetic detection sensor.

20 Claims, 9 Drawing Sheets

(51) Int. Cl.
 *G01R 33/28* (2006.01)
 *G01R 33/56* (2006.01)

(56) References Cited

U.S. PATENT DOCUMENTS

| | | |
|---|---|---|
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 2007/0060833 A1 | 3/2007 | Hauck |
| 2008/0183064 A1 | 7/2008 | Chandonnet et al. |
| 2012/0265054 A1 | 10/2012 | Olson |
| 2013/0066193 A1 | 3/2013 | Olson et al. |
| 2014/0275998 A1 | 9/2014 | Eichler et al. |
| 2016/0320210 A1* | 11/2016 | Nelson .................. A61B 5/062 |
| 2017/0209072 A1 | 7/2017 | Oren et al. |
| 2018/0116551 A1* | 5/2018 | Newman .............. A61B 8/0841 |
| 2018/0132938 A1* | 5/2018 | Everling .............. A61B 5/0044 |

\* cited by examiner

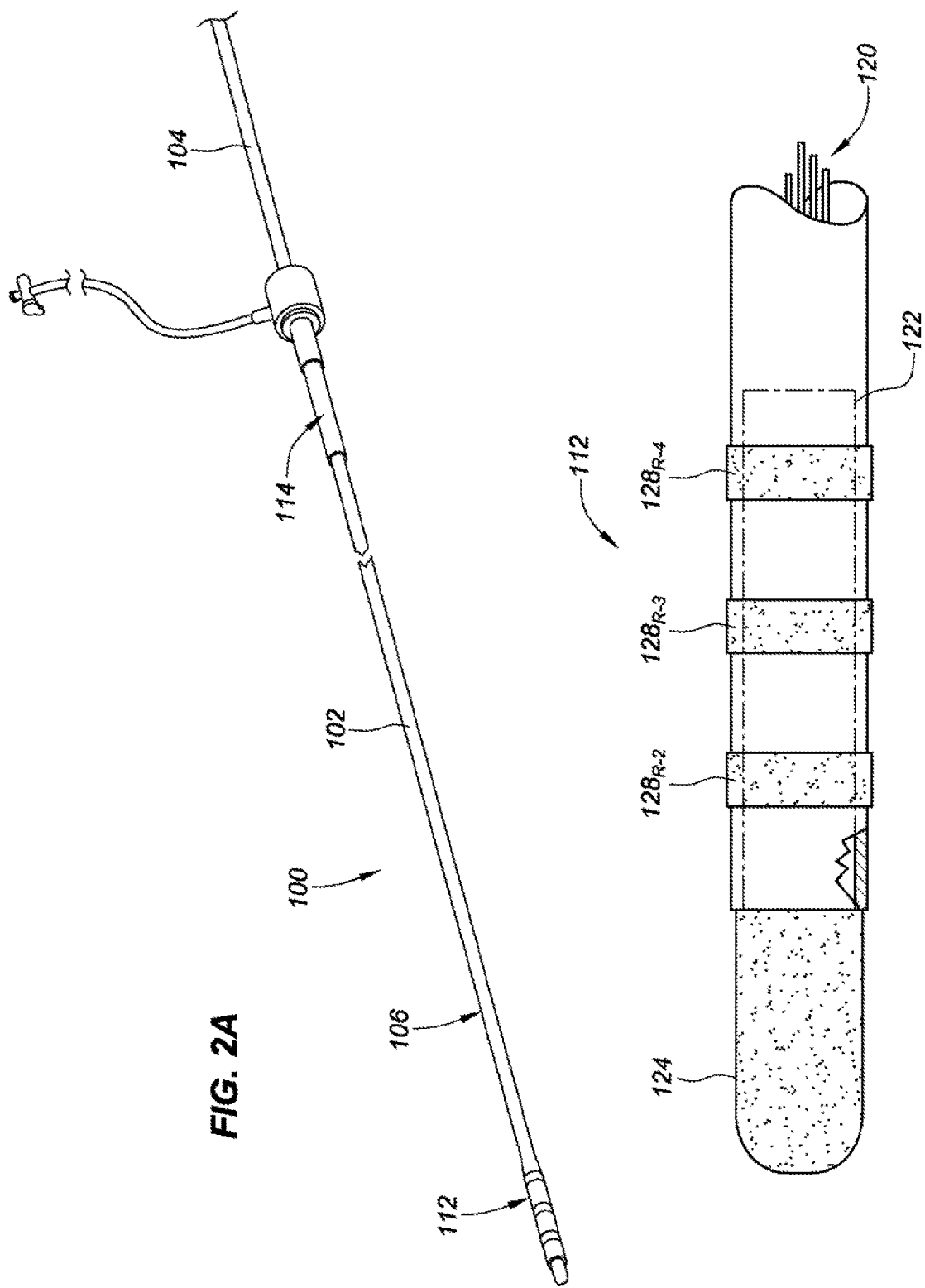

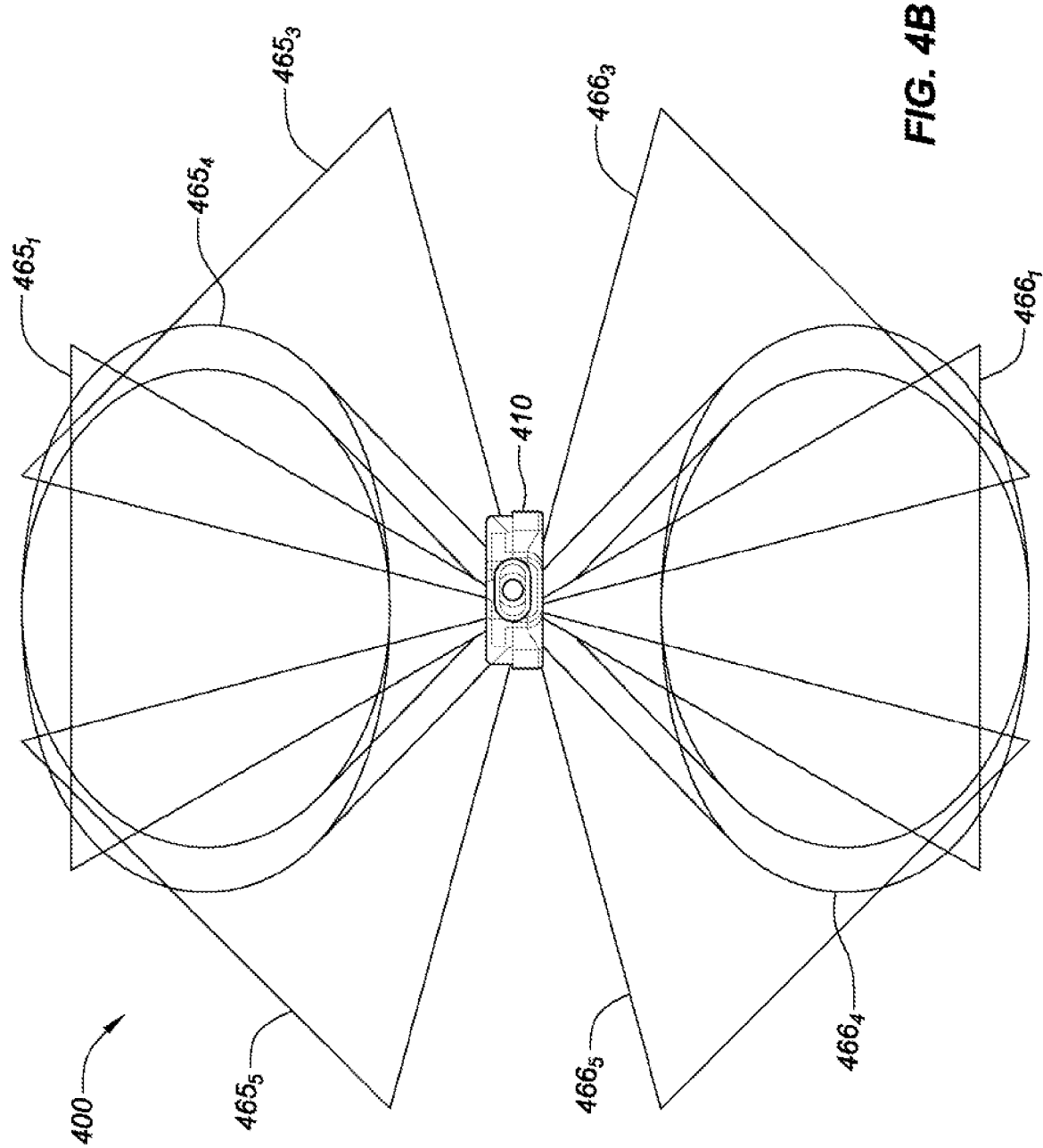

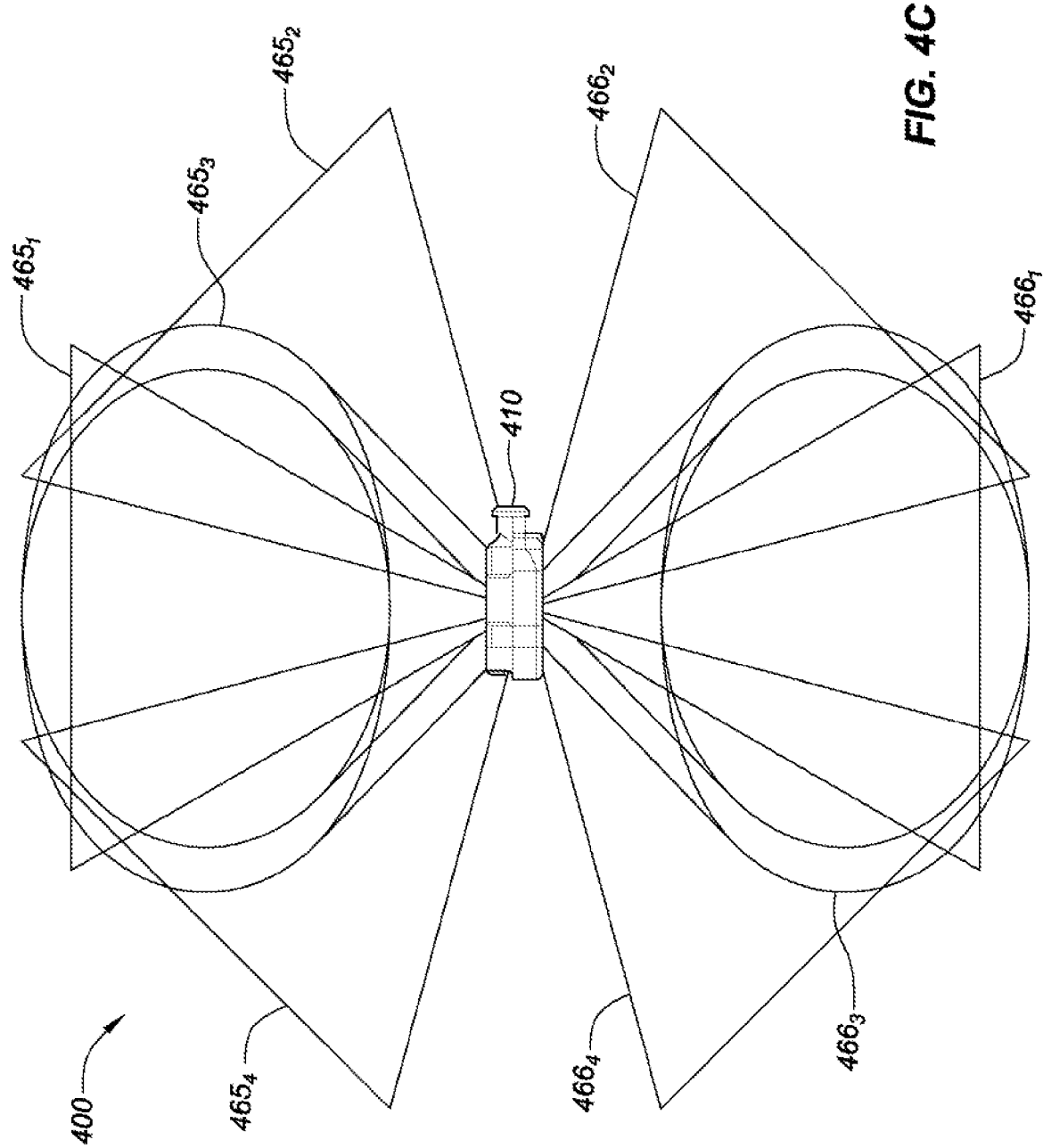

MAGNETIC FIELD DISTORTION DETECTION AND CORRECTION IN A MAGNETIC LOCALIZATION SYSTEM

CROSS-REFERENCE TO RELATED APPLICATIONS

This application is a national stage filing based upon International Application No. PCT/IB2020/053632, filed 16 Apr. 2020, which claims the benefit of U.S. provisional application No. 62/836,435, filed 19 Apr. 2019, which are hereby incorporated by reference as though fully set forth herein.

BACKGROUND a. Field

The present disclosure relates generally to the magnetic localization of medical instruments within a human body. More specifically, the instant disclosure relates to detecting magnetic field distortions within a magnetic field used for such magnetic localization systems.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature to the intended site, for example, a site within the patient's heart, and carries one or more electrodes, which may be used for diagnosis, mapping, ablation, or other treatments. Precise positioning of the catheter and clinician knowledge of the precise location within the body of the patient is desirable for improved procedure success rates.

To position a catheter within the body at a desired site, some type of localization must be used. To determine the relative position of the catheter to patient anatomy, magnetic localization systems have been developed that provide a location of the catheter within a well-known and controlled magnetic field. The externally-generated magnetic fields include precise magnetic gradients (field lines) that are sensed by the catheter (e.g., by elements such as coils) being located within the magnetic field. The currents induced by the magnetic field(s) in the sensing coils are analyzed using algorithmic processes and used to determine the position of the catheter within the patient's body. Once the catheter is positioned within the patient, as desired, a clinician may operate the catheter, for example, to ablate tissue to interrupt potentially pathogenic heart rhythms.

However, magnetic localization systems are susceptible to error induced by magnetic distortions within the magnetic field caused by, for example, extraneous ferrous or metallic objects intruding into the magnetic field. The introduction of such distortions may result in the system presenting an inaccurate position of the catheter within the patient's body. Such inaccurate catheter location data can limit the efficacy of a medical procedure.

The foregoing discussion is intended only as an exemplary illustration of the present field and is not intended to limit the claim scope.

BRIEF SUMMARY

Various embodiments of the present disclosure identify and correct for magnetic field distortions associated with the intrusion of metallic objects in a magnetic field used for localization of a medical device.

Aspects of the present disclosure are directed to a system for detecting magnetic distortion in a magnetic field used for localization of a catheter within a patient. The system includes a magnetic field generator and a magnetic detection sensor. The magnetic field generator generates the magnetic field for localization of the catheter within the patient. The magnetic detection sensor includes a plurality of sensor coils positioned at fixed distances and orientations relative to one another. Each of the sensor coils sense the magnetic field within a sensing region aligned with a longitudinal axis of the sensor coil, and outputs an electrical signal indicative of the sensed magnetic field. The plurality of sensing coils form two substantially contiguous sensing regions, a first continuous sensing region above the magnetic detection sensor, and a second continuous sensing region below the magnetic detection sensor. In more specific embodiments, the plurality of sensor coils includes a central coil and four peripheral sensor coils circumferentially surrounding the central coil.

Some embodiments of the present disclosure are directed to an apparatus for detecting electronic signals indicative of magnetic distortion in a magnetic field for localization of a catheter within a patient. The apparatus includes a central sensor coil that is vertically orientated, and a plurality of peripheral sensor coils circumferentially extending about the central sensor coil. Each of the sensor coils receive energy indicative of a magnetic field strength substantially coaxial with the sensor coil. Each of the peripheral sensor coils are positioned with substantially equal perpendicularity relative to an axis of the magnetic field. In more specific embodiments, the sensing coils form two substantially contiguous sensing regions, a first continuous sensing region above the apparatus, and a second continuous sensing region below the apparatus.

Additional features, advantages, and embodiments of the disclosure may be set forth or apparent from consideration of the detailed description and drawings. Moreover, it is to be understood that the foregoing brief summary and the following detailed description, drawings, and attachment are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure.

FIG. 2A is a fragmentary, isometric view of a catheter assembly comprising a catheter configured for localization in a magnetic localization system and an introducer, consistent with various aspects of the present disclosure.

FIG. 2B is an enlarged, fragmentary side view of the distal tip assembly of the catheter of FIG. 2A, consistent with various aspects of the present disclosure.

FIG. 4B is a front view of the magnetic detection sensor of FIG. 3A illustrating the sensing regions of each sensor coil, consistent with various aspects of the present disclosure.

FIG. 4C is a side view of the magnetic detection sensor of FIG. 3A illustrating the sensing regions of each sensor coil, consistent with various aspects of the present disclosure.

Figure 1:
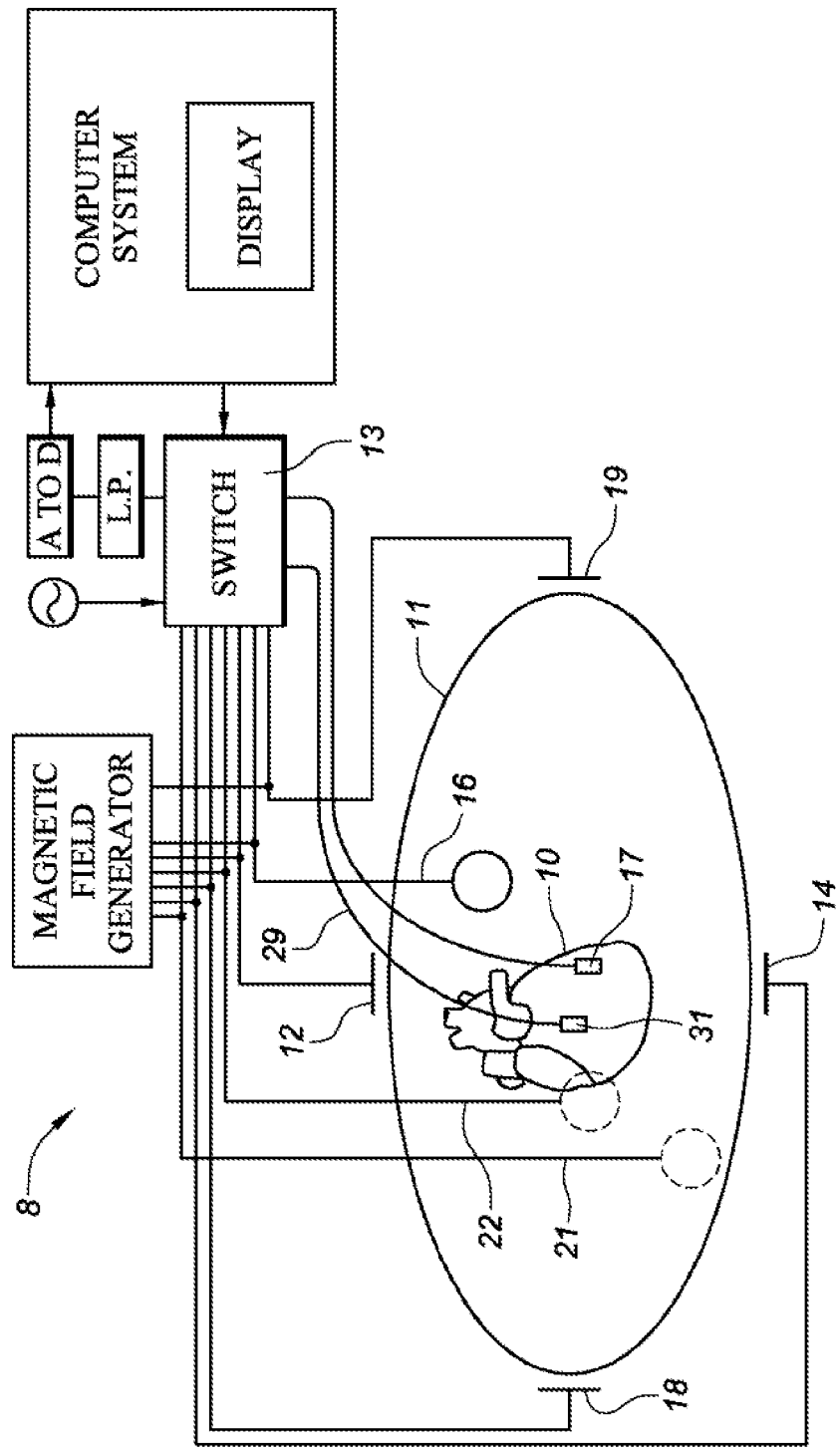
FIG. 1 is a schematic diagram of a magnetic localization system, consistent with various aspects of the present disclosure.

While various embodiments discussed herein are amenable to modifications and alternative forms, aspects thereof have been shown by way of example in the drawings and will be described in further detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

Cardiac localization systems are capable of displaying a three-dimensional (3D) position of conventional electrophysiology catheters within an overlaid model or image of a cardiac chamber, for example. These localization systems may also display cardiac electrical activity as waveform traces and as dynamic 3-D isopotential maps on the model of the cardiac chamber. The contoured surfaces of these three dimensional models may be based on the anatomy of the patient's own cardiac chamber. These localization systems may use impedance based and/or magnetic based localization technologies to render catheter position and facilitate model creation.

When using magnetic localization, the magnetic field(s) generated from a local source is inherently susceptible to distortions caused by metallic or ferrous objects intruding into, or being placed adjacent to, the generated magnetic field(s). Such distortions can cause inaccuracies in calculated or determined medical device locations, and in related anatomical models and other representations.

Magnetic sensors embedded within intracardiac catheters are used to determine position and orientation of the catheter with respect to one or more known reference positions. This magnetic position and orientation information can be used to navigate the catheter and can also be used to optimize impedance-based catheter localization (when the localization system is a hybrid-type system). When navigating catheters in magnetic space, the displayed or otherwise reported positions of the catheters can notably shift (e.g., visually shift on a screen displaying a representation of the location of the catheters) when the underlying magnetic field is changed/distorted despite no actual change (or minimal actual change) in the catheter's physical location. Understandably, this shift can cause inaccuracies to models created using the reported locations of the catheters. Embodiments of the present disclosure, as described in more detail below with reference to the figures, identify the existence of such distortions within a magnetic field.

In magnetic-field based localization system, a magnetic detection sensor may be tracked positionally within a generated magnetic field. The sensor coils of the magnetic detection sensor are sensitive to instability and inaccuracies associated with weakened magnetic field signals in certain regions of the generated magnetic field and distortions in the magnetic field due to the ingress of ferrous materials. In various embodiments of the present disclosure, a magnetic detection sensor is disclosed including a novel out-of-plane configuration of five magnetic sensor coils which increases the sensitivity of the navigation system to detect and correct for distortions in the magnetic field, and thereby increases the robustness of the system in compromised environments. The magnetic detection sensor may include four perimeter sensor coils that are oriented perpendicular relative to one another, as well as a fifth sensor coil positioned vertically at the center of the other four sensing coils. The sensor coils of the magnetic detection sensor are secured within a housing in such a way that proximal ends of each of the four perimeter sensor coils lie in a first common plane, and distal ends of each of the perimeter sensor coils lie in a second common plane. The perimeter sensor coils of the magnetic detection sensor are positioned such that the axis of each sensor coil is out of alignment with an emitted magnetic field. It has been discovered that prior art magnetic reference sensors in magnetic-field based localization systems suffer from orientation specific error associated with alignment of one or more of the sensor coils and the generated magnetic field. Specifically, where one of the sensor coils is aligned with the generated field, in response to a magnetic-field distortion, the calculated position error of that sensor coils is significant. To compensate for the error in the magnetic position calculation associated with the magnetic-field distortion, a transfer function may be calculated based on the actual spatial relationship of the sensor coils (fixed and known position and orientation) and the perceived spatial relationship of the sensor coils by the localization system. The transfer function may then be applied to the sensed position of, for example, a distal tip of an intravascular catheter within a patient's vasculature to correct for any error in the sensed position due to the magnetic-field distortion.

It has been discovered, for example, that metal plates within an electrophysiology catheter lab have a large effect on magnetic detection sensors when the metal plates are positioned with an orientation within 30° of perpendicular to a sensing axis of a sensor coil. Aspects of the present disclosure maximize detection and measurement of magnetic field distortions (e.g., eddy currents), independent of the relative orientation of the field distorting object to the sensor coils. In prior art magnetic detection sensors, the sensor would exhibit variable sensitivity to magnetic distortions based on the yaw orientation of the sensor to the field distorting object. As a result, the error rate of prior art localization systems exhibited variable position detection error rates of a catheter depending on the yaw orientation of a magnetic detection sensor relative to the field distorting object.

Aspects of the present disclosure disclose a magnetic detection sensor with a novel configuration of five sensor coils (e.g., magnetic barrel sensors) to optimize the measurement of distortions within a magnetic field for a localization system. The localization system compensating for the measured distortions on other tracked elements within the magnetic field, where the compensation to the magnetic distortion induced error on the position and orientation of the tracked elements are independent of the relative yaw orientation of the tracked elements relative to the field distorting object(s).

Embodiments presented below utilize a magnetic detection sensor with a sensor coil configuration which maximizes a detection window of magnetic-field distortion.

FIG. 1 shows a schematic diagram of a magnetic localization system 8 used for navigating the human anatomy of a patient 11 (depicted, for simplicity's sake, as an oval in FIG. 1) while conducting a medical procedure. For example, as shown in FIG. 1, the system 8 may be used to map a heart 10 of the patient and to navigate a cardiac catheter through the chambers of the heart. Magnetic localization system 8 determines the location (and, in some embodiments, the orientation) of objects (e.g., a portion of a diagnostic or ablation catheter, such as the electrode assembly 112 depicted in FIGS. 2A and 2B), typically within a three-dimensional space, and expresses those locations as position information determined relative to at least one reference. Specifically, the magnetic localization system 8 may be used to determine the location of the cardiac catheter within a magnetic field, which is then overlaid onto, for example, an image or a model of the heart 10. In other embodiments, magnetic resonance imaging data, among other reference data may be overlaid onto the three-dimensional space to provide a clinician with a virtual work environment in which to reference for real-time position of the cardiac catheter relative to the patient's heart 10.

The magnetic localization system 8 may include various visualization, localization, mapping, and navigation components. For example, the localization system 8 may comprise a magnetic-field-based system such as the CARTO™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the localization system 8 may comprise a magnetic field based system such as the MEDIGUIDE™ Technology system available from St. Jude Medical, Inc., and as generally shown with reference to one or more of U.S. Pat. Nos. 6,233,476; 7,197,354; 7,386,339; U.S. patent application Ser. No. 14/208,120 entitled "Medical Device Navigation System" filed on 13 Mar. 2014, U.S. Provisional Patent Application No. 61/834,223 entitled "Medical Device Navigation System" filed on 12 Jun. 2013, and International Application No. PCT/M2014/059709 entitled "Medical Device Navigation System" filed on 13 Mar. 2014, the disclosures of which are hereby incorporated by reference in their entireties as though fully set forth herein. In yet another embodiment, the localization system 8 may comprise a hybrid-type system (i.e., electric-field-based and magnetic-field-based system), such as, for example and without limitation, the EnSite Precision™ system of St. Jude Medical, Inc., and the systems described in pending U.S. patent application Ser. No. 13/231,284 entitled "Catheter Navigation Using Impedance and Magnetic Field Measurements" filed on 13 Sep. 2011 and U.S. patent application Ser. No. 13/087,203 entitled "System and Method for Registration of Multiple Navigation Systems to a Common Coordinate Frame" filed on 14 Apr. 2011, each of which is hereby incorporated by reference in its entirety as though set fully forth herein, or the CARTO™ 3 system commercially available from Biosense Webster. In yet still other exemplary embodiments, the localization system 8 may comprise or be used in conjunction with other commonly available systems, such as, for example and without limitation, fluoroscopic, computed tomography (CT), and magnetic resonance imaging (MRI) based systems. For purposes of clarity and illustration only, the localization system 8 will be described hereinafter as comprising a magnetic-based localization system.

Various embodiments of the present disclosure may include various visualization, mapping and navigation components as known in the art, including, for example, an EnSite Precision™ System commercially available from St. Jude Medical, Inc., or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application). The '397 patent and the '580 application are both hereby incorporated by reference as though fully set forth herein.

FIG. 1 may further exemplify a hybrid localization system including both an impedance-based localization system and a magnetic-based localization system.

In general, and as shown in FIG. 1, localization system 8 includes a plurality of magnetic field transmitters (e.g., one or more of 12, 14, 16, 18, 19, and 21) that emit a magnetic field across the patient's body 11. These magnetic field transmitters, which may be placed upon or attached/applied to the patient, or fixed to an external apparatus, define three generally orthogonal axes (e.g., an x-axis, a y-axis, and a z-axis). The magnetic field transmitters are electrically coupled to a magnetic field generator. The magnetic field generator generates one or more magnetic fields that may be transmitted simultaneously, time multiplexed, and/or frequency multiplexed via the magnetic field transmitters. A switch 13 samples the signals received from one or more of receivers (e.g., one or more of 17, 22, and 31; a catheter, a patient reference sensor, an internal reference sensor, a magnetic detection sensor, etc.). The received signals from the receivers, indicative of the magnetic field that traversed through the patient's body 11 from one or more of the transmitters, are then converted from an analog to a digital signal for further processing by the computer system 97. The computer system 97 may include processor circuitry 99 which comprises hardware/software modules for performing computations on the data received from the receivers. The processor circuitry determining, for example, the location of a cardiac catheter within the patient's heart. However, the actual catheter position may be obscured by magnetic distortions within the magnetic field caused by other ferrous/metallic bodies. These magnetic distortions are associated with an error rate of the perceived position of the catheter compared to the actual position of the catheter. In accordance with various aspects of the present disclosure, the processor circuitry 99 may determine a position error associated with magnetic distortion, and calculate a corrected position for the various sensor coils.

For reference by a clinician during a procedure, the perceived location of the catheter within the magnetic field can be presented on a display 98 in relation to known reference points, e.g., cardiac chambers, arteries, etc.

For purposes of this disclosure, an example application of the localization system may be a medical device, such as a catheter, which extends into the left ventricle of the patient's heart 10. The catheter includes a plurality of sensor coils spaced along its length. As used herein, the term "sensor coils" generically refer to any element (e.g., magnetic sensors) whose position within a magnetic field can be measured by that system. The localization system, where all of the sensor coils lie within the magnetic field, may collect localization data from all of the sensor coils simultaneously.

A magnetic-based localization system 8 may include a fixed reference 22 (e.g., a magnetic detection sensor) to define the origin of the magnetic-based localization system's coordinate frame. This fixed reference provides a relative position to which the positions of sensor coils on the catheter are measured. Such a fixed reference can likewise be in a fixed internal or external location. Likewise, multiple references may be used for the same or different purposes (e.g., to correct for respiration, patient shift, system drift, or the like).

A computer system 97, which can comprise a conventional general-purpose computer, a special-purpose computer, a distributed computer, or any other type of computer, and which can comprise one or more processors, such as a single central processing unit (CPU), or a plurality of processing units, commonly referred to as a parallel processing environment, may control magnetic localization system 8 and/or execute instructions to practice the various aspects of the embodiments described herein.

FIG. 2A is a simplified, isometric view of an exemplary catheter assembly 100 that can be used in conjunction with system 8. In some embodiments, and as shown in FIG. 2A, the catheter assembly 100 comprises a catheter 106 that includes a catheter tip assembly (also referred to as an electrode assembly or distal tip assembly) 112 at a distal end portion and operatively adapted for conducting a diagnostic or a therapeutic procedure under clinician control. A proximal end portion 104 of the catheter 106 may include a steering handle or other mechanism (not shown). In the present embodiment, catheter 106 is a mapping catheter. The catheter 106 includes a flexible shaft 102 extending between the proximal end portion 104 and the catheter tip assembly 112. The catheter assembly 100 further includes an electrical connector (not shown) configured to establish electrical connection(s) between the catheter tip assembly 112 and external electrical components (not shown) to perform, for example, localization, mapping, ablation, and/or pacing procedures. FIG. 2A further shows an introducer 114 comprising part of the catheter assembly 100. The catheter tip assembly 112 may comprise a plurality of sensors coils (also referred to as localization coils or sensors) such as those shown, for example, in U.S. Pat. No. 6,690,963 (see, e.g., sensors 30, 32, 34 depicted in FIGS. 2 and 3), which has been incorporated herein by reference. These sensor coils may be located, for example, in the region shown by the dashed box 122 in FIG. 2B.

FIG. 2B is an enlarged, side view showing, in greater detail, the tip assembly 112. The tip assembly 112 includes a tip electrode 124, a plurality of ring electrodes $128_{R-2}$, $128_{R-3}$, and $128_{R-4}$, and a plurality of electrical conductors 120 (e.g., one conductor electrically connected to each of the three ring electrodes and a separate conductor electrically connected to the tip electrode 124). Additional electrical connectors may extend proximally from the tip assembly 112 if localization coils are located in, for example, the area outlined by dashed box 122. While aspects of the present disclosure refer to a mapping catheter, it is to be understood that various other types of catheter may be utilized in the localization system described herein.

Figure 3A:
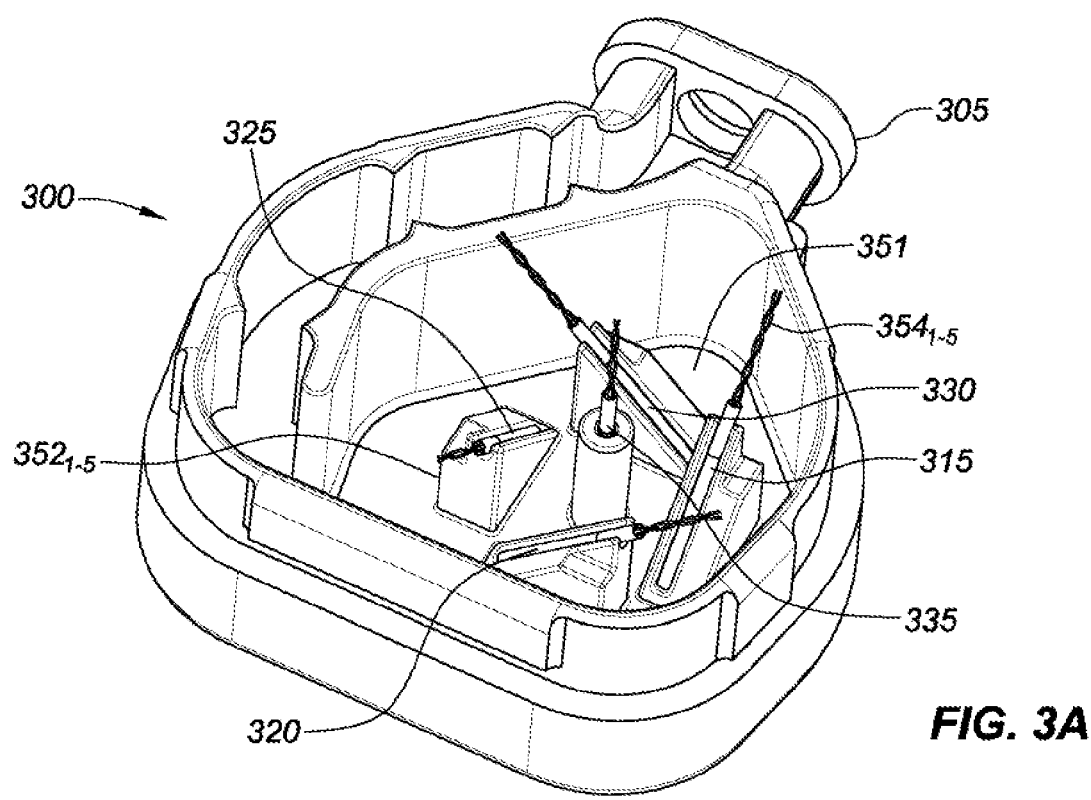
FIG. 3A is an isometric top view of a magnetic detection sensor, consistent with various aspects of the present disclosure, with portions of the sensor housing broken away to reveal internal features.
Figure 3B:
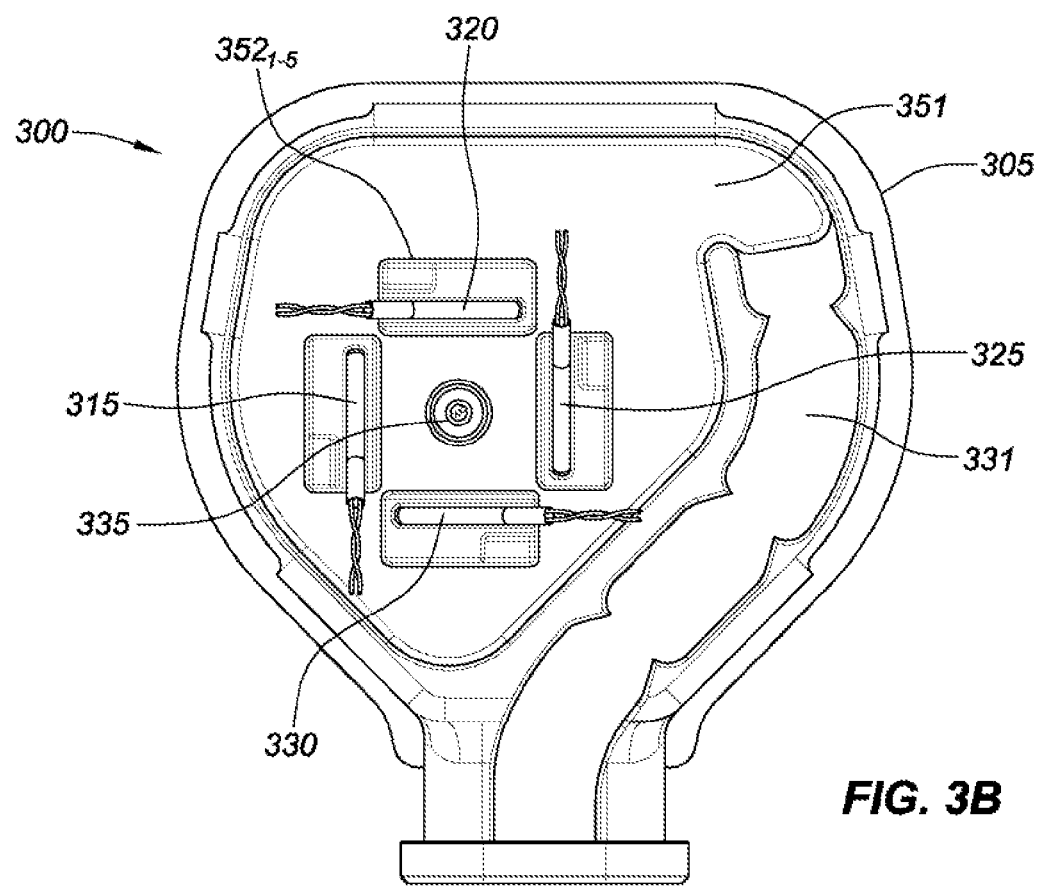
FIG. 3B is a top view of the magnetic detection sensor of FIG. 3A, consistent with various aspects of the present disclosure.

FIG. 3A is an isometric top view of a magnetic detection sensor 300 and FIG. 3B is a top view of the magnetic detection sensor 300 of FIG. 3A, consistent with various aspects of the present disclosure. Both FIGS. 3A and 3B show the sensor housing 305 with portions broken away to reveal internal features and components. The sensor housing 305 houses five sensor coils via channels $352_{1-5}$. For example, a first sensor coil 315 may be placed into channel $352_1$. Once positively positioned within the respective channels, each of the sensor coils may be secured to the housing 305 using, for example, adhesive. As shown in FIGS. 3A and 3B, four of the sensor coils 315, 320, 325, and 330 circumferentially extend about a central, vertically oriented, sensor coil 335. The four peripheral sensor coils 315, 320, 325, and 330 are positively positioned by the channels so that a distal end of each of the sensor coils are within a first common plane, and a proximal end of each of the sensor coils are within a second common plane. Further the channels 352 positively position the longitudinal axis of each of the four peripheral sensor coils 315, 320, 325, and 330 at a right angle relative to one another. As further shown in FIG. 3C, each of the peripheral sensor coils are oriented 45° relative to a surface 351 of the sensor housing 305. Further, in the present embodiment, each of the five sensor coils have a center point which fall within the same plane.

The configuration of the five sensor coils in the magnetic detection sensor 300 forms a symmetric detection umbrella above and below the sensor that accurately and completely measures the local magnetic field (and distortions therein), as shown in more detail in reference to FIGS. 4A-C.

While various different embodiments for precisely positioning the sensor coils within the cavity 331 are readily envisioned by a skilled artisan, the present embodiment utilizes channels $352_{1-5}$, and an adhesive application to secure the sensor coils to sensor housing 305.

Lead wires $354_{1-5}$ extend out from a proximal end of each of the sensor coils 315, 320, 325, 330 and 335, and may be routed through cavity 330 of sensor housing 305 before exiting the housing (in a common wiring bundle). In some embodiments cavity 330 of sensor housing 305 may be potted to further prevent displacement of the sensor coils relative to one another.

In the present embodiment, each of the sensor coils 315, 320, 325, 330 and 335 are affixed in orthogonal orientations relative to one another. During operation, the magnetic detection sensor 300 is placed within a generated magnetic field and each of the respective sensor coils receive energy indicative of the strength and orientation of the magnetic field. In one specific embodiment, a vector sum of the received energy is computed to determine a perceived change in the position of the sensor coils relative to one another. A perceived change being indicative of a magnetic distortion in the magnetic field proximal the magnetic detection sensor. In medical magnetic localization applications, such magnetic distortions affect the ability of the system to accurately determine a position of, for example, a catheter within a patient's body.

In some embodiments, sensor housing 305 may further house electronic circuitry which may conduct a number of signal processing functions including, e.g., analog-to-digital conversion, pre-amplification, and signal noise filtration. Accordingly, before transmitting the received signals from sensor coils 315, 320, 325, 330 and 335 to computing circuitry for processing and determination of the amount of distortion in the magnetic field, the raw signals from each of the sensor coils may be conditioned. After signal processing, the received sensor coil signals are transmitted to the processor circuitry of the magnetic localization system for determination of the sensed position of each of the sensor coils within the magnetic detection sensor 300. In further embodiments, the magnetic detection sensor 300 may wirelessly transmit the received signals from each of the sensor coils to the processor circuitry of the magnetic localization system using wireless data transmission protocols known to one of skill in the art.

To facilitate magnetic distortion detection and correction, the localization processing circuitry determines, based on the received signals from each of the sensing coils, a perceived location/orientation of each of the sensing coils. As the actual location/orientation of each of the sensing coils relative to one another is known, a transfer function may be calculated which corrects for the magnetic distortion causing the error between the actual and sensed locations of the coils relative to each other. This transfer function may then be used for other sensing coils within the same magnetic field to correct for the sensed distortion thereto.

Figure 3C:
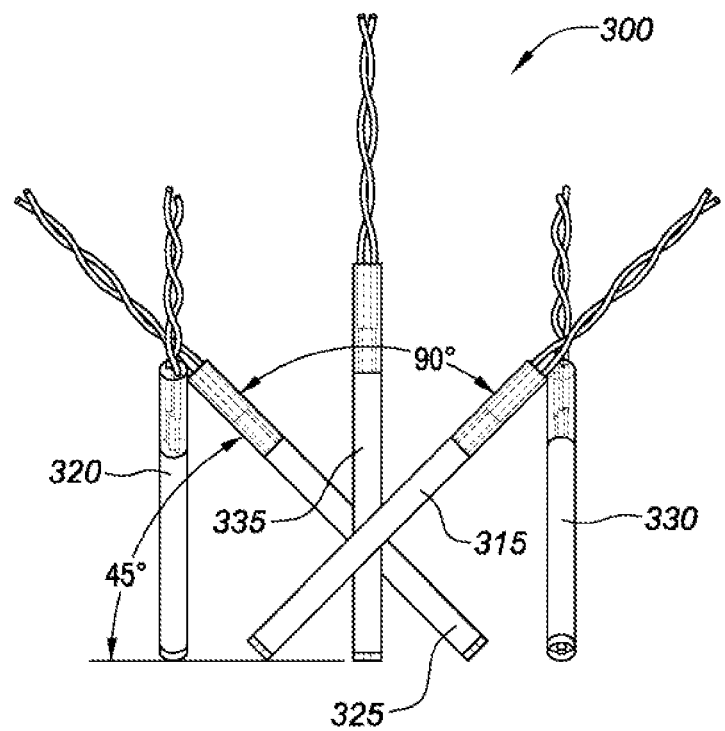
FIG. 3C is a close-up, side view of five sensing coils of the magnetic detection sensor of FIG. 3A, consistent with various aspects of the present disclosure.

FIG. 3C shows a side view of the sensor coils of the magnetic detection sensor 300 of FIG. 3A. As shown in FIG. 3C, peripheral sensor coils 315, 320, 325, and 330 are oriented orthogonal to one another and affixed at known distances from each other. Each of the peripheral sensor coils are also angled 45° relative to a horizontal surface of the sensor housing. Central coil 335 is oriented vertically. During operation of the magnetic detection sensor in a magnetic field, the output of the sensor coil array is used to calculate magnitude positions and orientations associated with the mechanical position and orientation of the sensor coils relative to one another.

In one specific embodiment of a localization system in accordance with the present disclosure, a vector sum of the distances are calculated between the centers of the longitudinal axes of the five sensor coils. In response to a distortion in the magnetic field, the perceived location of one (or more) of those sensor coils may be displaced from its known/fixed location relative to the other sensor coils. As a result, the corresponding vector sum would be correspondingly affected. A change in the vector sum from the initial index value, above a determined threshold, is indicative of a distortion to the generated magnetic field which renders the position determination of the localization system unreliable. After determining an initial index-value (where the magnetic field is free of distortions), subsequent magnitude positions and orientations may be correlated timewise. These later magnitude values may vary from the initial index-value due to localized magnetic distortions within the magnetic field, resulting in a perceived skewing of the location and orientation of the sensor coils relative to one another (even though the orientation and position of the sensor coils to one another are fixed). The initial index-value may be compared to subsequent index-values to determine when acceptable levels of magnetic field distortion during a medical procedure are exceeded. This delta value (the change in value between the initial index-value and a subsequent index-value) is associated with distortion related drift in the localization of the magnetic detection sensor coils.

In one example application of a magnetic detection sensor in a localization system, an acceptable delta value for magnetic distortion may be determined by the clinician (e.g., a soft threshold value), and/or the processor circuitry (e.g., a hard threshold value). In such an embodiment, the magnetic localization system may indicate that a distortion is affecting the perceived location of the catheter within the patient upon exceeding the soft threshold value, but continue displaying the perceived location of the catheter on the display. Where the delta value of the index-value exceeds a hard threshold value, the magnetic localization system may no longer update the display with the newly-calculated perceived location of the catheter due to the inaccuracy of the location information. Once the calculated index-value falls back below the hard threshold value, the magnetic localization system will resume updating the display with the perceived location of the catheter within the patient. In yet further embodiments, and in accordance with the various embodiments presented above, the localization system may correct for the location error of the catheter and display the corrected location of the catheter (and the uncorrected position).

Figure 3D:
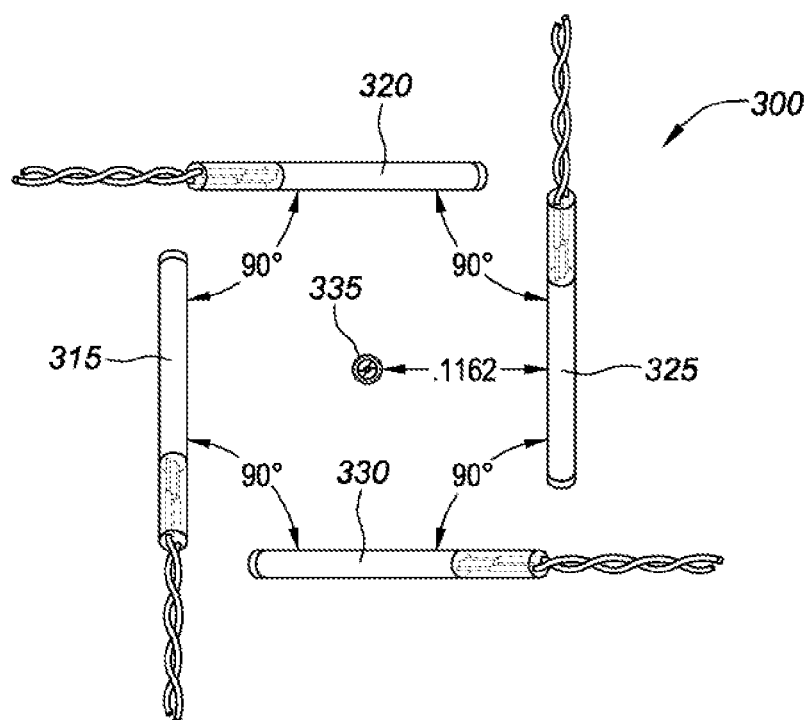
FIG. 3D is a close-up, top view of five sensing coils of the magnetic detection sensor of FIG. 3A, consistent with various aspects of the present disclosure.

As shown in FIG. 3D, each of the opposing peripheral sensor coils 315, 320, 325, and 330 are orientated orthogonal to one another. Accordingly, each of the peripheral sensor coils is oriented planar to one of three dimensional axes, and receives magnetic field energy that is substantially co-axial with the sensor coil. A center coil 335 is vertically oriented at a center point of the sensor coil array. Each of the peripheral sensor coils are positioned approximately 0.1" away from the center coil 335. In some specific embodiments, such as FIG. 3D, the peripheral sensor coils are positioned 0.1162" away from the center coil 335. As evident in the top view of the sensor coils, each of the adjacent peripheral sensor coils are orthogonally positioned relative to one another about the center coil 335.

In view of the above embodiment, a skilled artisan will appreciate that various other 5 coil magnetic detection sensor configurations may be implemented to achieve desirable sensitivity to magnetic distortions. While the various embodiments of magnetic detection sensors disclosed herein are generally directed to 5 sensor coil configurations, depending on the sensitivity characteristics of the sensor coils utilized in the array, sensor arrays with more or less sensors are readily envisioned. Importantly, and as discussed in more detail below, it is desirable for the magnetic detection sensor to have a substantially continuous hemispherical sensing field so that the sensor is not susceptible to variable distortion detection due to the relative alignment of one of the sensor coils to the field anomaly. It is to be understood that various other relative configurations and orientations of the sensor coil array may also be utilized.

As shown in FIGS. 3C and 3D, each of the peripheral sensor coils are arranged orthogonal to one another. As a result, when a top/bottom surface of the magnetic detection sensor 300 is oriented perpendicular to a central axis of a magnetic field, a longitudinal axis associated with each of the peripheral sensor coils will have substantially equal non-perpendicularity to the generated field.

Figure 4A:
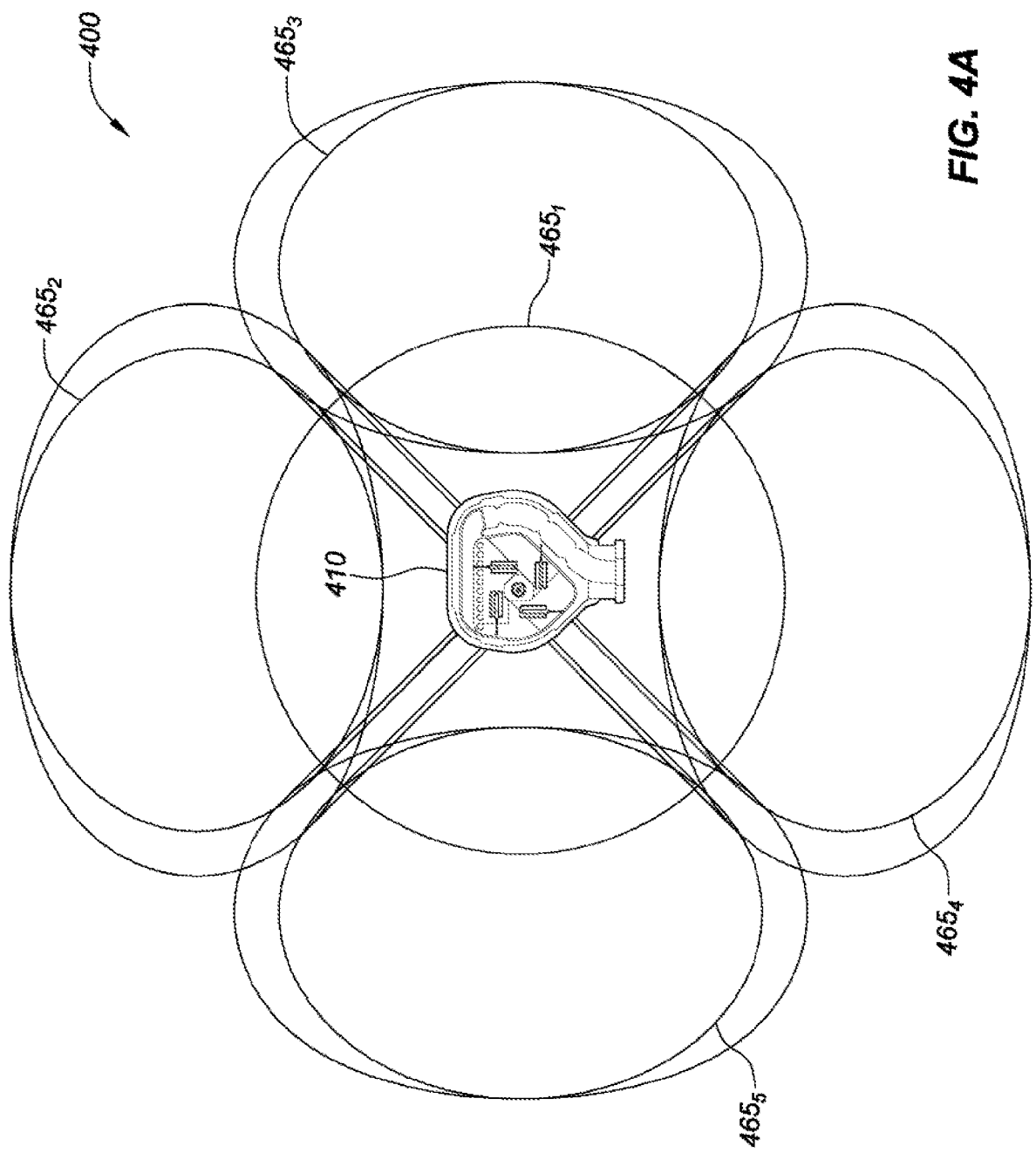
FIG. 4A is a top view of the magnetic detection sensor of FIG. 3A illustrating the sensing regions of each sensor coil, consistent with various aspects of the present disclosure.

FIG. 4A is a top view of the magnetic detection sensor 410 of FIG. 3A, FIG. 4B is a front view of the magnetic detection sensor of FIG. 3A, and FIG. 4C is a side view of the magnetic detection sensor of FIG. 3A. FIGS. 4A-C illustrating the sensing regions $465_{1-5}$, $466_{1-5}$ of each sensor coil, and thereby the resulting sensitivity of the magnetic detection sensor 410 as a whole. Particularly, upper hemisphere sensitivity is illustrated by the individual sensing regions $465_{1-5}$, and lower hemisphere sensitivity is illustrated by the individual sensing regions $466_{1-5}$. The sensing region of each sensor coil, in the present embodiment, extends radially outward at an angle of approximately 30° from a longitudinal axis of the coils. The relative position and orientation of the sensor coils in the magnetic detection sensor 410 results in a (nearly) contiguous sensing region in both the upper and lower hemispheres about the sensor.

Figure 5A:
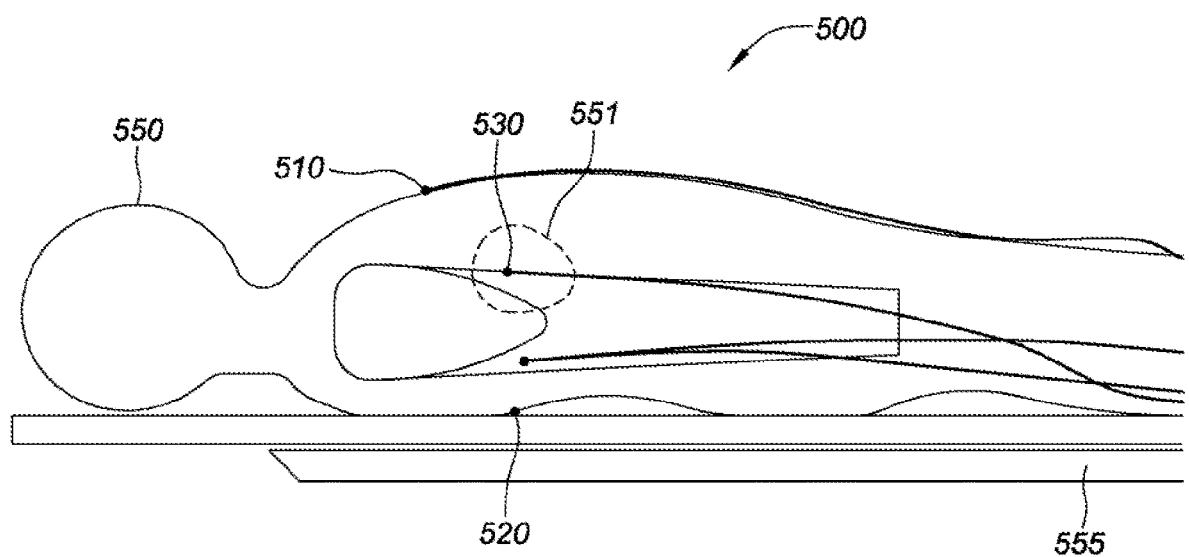
FIG. 5A is a side view of an example application of a magnetic detection sensor during a medical procedure, consistent with various aspects of the present disclosure.

FIG. 5A shows an exemplary placement of two magnetic detection sensors 510 and 520 relative to a patient 550 during a medical procedure where magnetic localization of a medical device within a patient is utilized (e.g., a cardiac ablation procedure). In the present embodiment, the first magnetic detection sensor 510 is placed anterior to the patient 550 (e.g., on a patient's chest), while a second magnetic detection sensor 520 is placed posterior to the patient (e.g., between a patient's back and an operating table 555). In many exemplary embodiments, the first and second magnetic detection sensors are ideally located adjacent (and opposite one another) to the anatomy of the patient where the procedure is being conducted. As shown in FIG. 5A, the first and second magnetic detection sensors are opposite one another relative to the heart 551, which is receiving treatment by way of catheter 530, which is extended into the heart. One or more magnetic field transmitters adjacent the patient emit a magnetic field used to determine the position of the catheter. Specifically, the catheter, including one or more sensor coil in a distal tip region, senses the magnetic field in proximity to the one or more coils. Processing circuitry can then determine, based on the sensed magnetic field at the tip of the catheter, where the one or more coils are located in the magnetic field and, therefore, where the tip of the catheter is located. However, egress of other ferrous objects into the magnetic field create magnetic distortions that affect localization of the catheter within the field. Accordingly, the first magnetic detection sensor 510 detects magnetic distortions in proximity to the anterior of the patient (e.g., medical instruments and equipment), and the second magnetic detection sensor 520 detects magnetic distortions in proximity to the posterior of the patient (e.g., ferrous objects associated with the operating room table, or other objects in the magnetic field there below). In such a configuration, magnetic distortions can be identified and a determination can be made as to the effect of the magnetic distortion on the catheter (e.g., whether the magnetic field in proximity to the catheter is being excessively affected by the magnetic distortion).

Figure 5B:
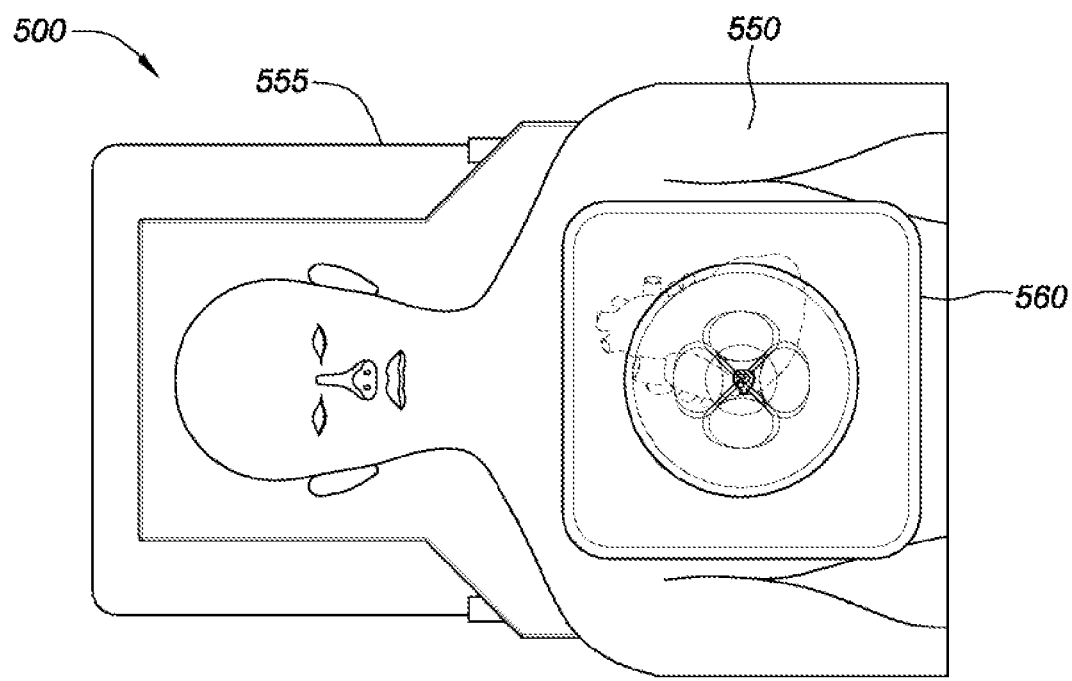
FIG. 5B is a top view of the example application of the magnetic detection sensor of FIG. 5A, consistent with various aspects of the present disclosure.
Figure 5C:
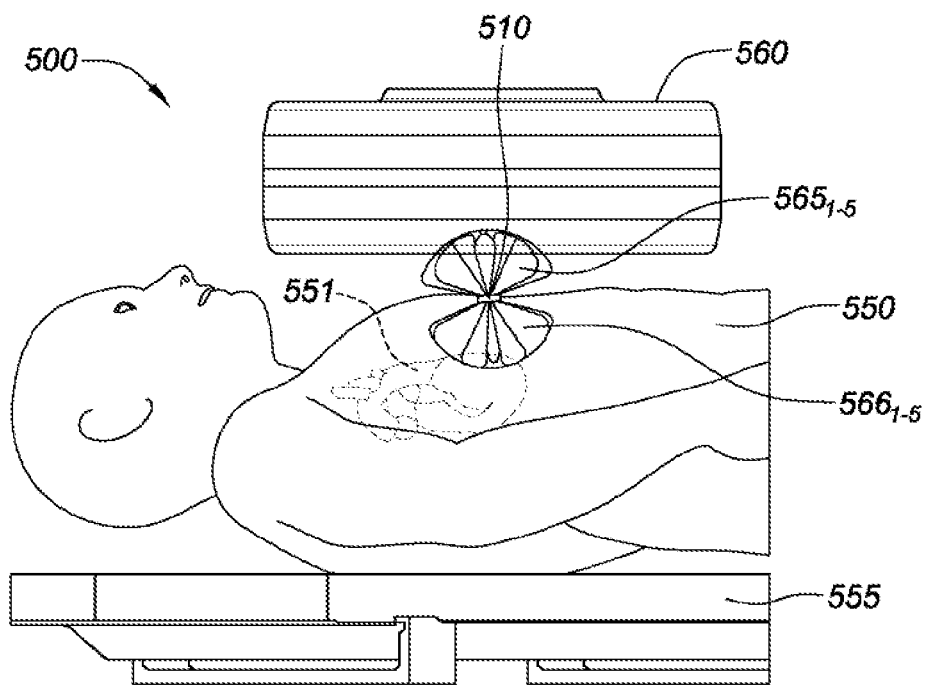
FIG. 5C is a side view of the example application of the magnetic detection sensor of FIG. 5A further illustrating a fluoroscopic imaging C-arm, consistent with various aspects of the present disclosure.

FIG. 5B is a top view of the magnetic detection sensor application 500 of FIG. 5A, and FIG. 5C is a side view of the magnetic detection sensor application 500 of FIG. 5A. FIGS. 5B and 5C further illustrating a fluoroscopic imaging C-arm 560, consistent with various aspects of the present disclosure. During an intravascular catheter procedure, for example, the fluoroscopic imaging system may be used as a secondary catheter localization means. During fluoroscopic imaging, the C-arm 560 is positioned in close proximity to a target area for imaging (e.g., a patient's heart 551). As shown in FIGS. 5B and 5C, a magnetic detection sensor 510 is placed between the C-arm 560 and the patient 550. It has been discovered that a C-arm may introduce a substantial magnetic distortion to the generated magnetic field for localization (due to the large amount of metal forming the C-arm). As such, it is desirable to position the magnetic detection sensor 510 between the C-arm and the patient 550 to enhance detection of such distortions associated with the C-arm. Sensing regions 565$_{1-5}$ are well positioned to detect such C-arm distortions. Sensing regions 566$_{1-5}$ are directed toward the patient 550 and facilitate detection of distortions in proximity to the operating table 555, for example.

In various embodiments of the present disclosure, to prevent inaccuracies in a magnetic localization system, the magnetic localization system may utilize one or more of the magnetic distortion sensors to determine a variance between actual locations (based on the known/fixed position of the magnetic distortion sensor within the system) and perceived locations (those determined based on the received magnetic fields at the magnetic distortion sensor and post-processing). The determined variance is indicative of magnetic distortion throughout the magnetic field due to egress of ferrous/metallic objects into the magnetic field. Based on the variance at each of the magnetic distortion sensor locations, a transform may be computed to correct for the distortion at all locations within the magnetic field, including the magnetic distortion experienced by the medical device being magnetically localized.

In various embodiments of a magnetic detection sensor, in accordance with the present disclosure especially in embodiments where fluoroscopy or other X-ray type imaging is required (during a medical procedure), the sensor may include materials that are transparent to X-ray imaging, and/or shaped to prevent interference with such imaging.

In various embodiments of the present disclosure, one or more magnetic distortion detection sensors may be implemented in a hybrid-type localization system, such as the EnSite™ Precision™ Electro Anatomical Mapping System commercially available from St. Jude Medical, Inc. In such a configuration, impedance measuring patches are electrically coupled to the patient (e.g., on a patient's chest, on either side of patient's chest, and/or on at least one of patient's legs). Based on the varying impedance values detected by the impedance measuring patches, an impedance-based location of the medical device may be determined.

In various embodiments of the present disclosure, the magnetic detection sensor enables improved accuracy within a localization system by indicating when a location of the medical device provided by the magnetic field-based localization sub-system is inaccurate due to a magnetic distortion. In response, the mapping system may ignore the location data from the magnetic field-based portion of the system, or correct for the distortion using one or more of the methods disclosed herein. For example, data from one or more of the magnetic distortion sensors may be used to determine a variance between actual locations (based on the known/fixed position of the magnetic distortion sensor within the system) and perceived locations (those determined based on the received magnetic fields at the magnetic distortion sensor and post-processing). The determined variance is indicative of magnetic distortion throughout the magnetic field due to egress of ferrous/metallic objects into the magnetic field. Based on the variance at each of the magnetic distortion sensor locations, a transform may be computed to correct for the distortion at all locations within the magnetic field, including the magnetic distortion experienced by the medical device being magnetically localized.

In further more specific embodiments of the present disclosure, and consistent with all the above embodiments, magnetic distortion sensors (and the sensor coils therein) may also be utilized to compensate for the sensed magnetic distortion. To compensate for magnetic distortion in the magnetic localization system, the fixed locations of the magnetic distortion sensors provide a fixed reference frame. Based on the variance between the actual position (a known position or a position detected during calibration) and the perceived location of each of the magnetic distortion sensors based upon the sensed magnetic field, the effect of the magnetic distortion throughout the magnetic field may be calculated and represented by a transform that restores the perceived locations of each of the magnetic distortion sensors back to the respective actual positions. Similarly, the transform may be applied to the perceived location of a medical device within the magnetic field to determine a corrected (actual) location of the medical device.

Where an actual location of a magnetic distortion sensor in a reference frame is not known (such as where the sensor is fixed to the patient), the relative location of the magnetic distortion sensor to another magnetic distortion sensor, where the distance between the two magnetic distortion sensors is fixed, can also be relied upon to correct for magnetic distortion in a magnetic localization system. The transform in such an embodiment being based upon a variance between the actual distances between the magnetic distortions sensors and the perceived distances between the magnetic distortions sensors based upon the sensed magnetic field at each of the magnetic distortion sensors. The calculated transform may then be used to correct the perceived location of the medical device.

In embodiments such as those presented herein, the magnetic distortion sensors are generally centered about the portion of the patient's body where the medical device localization is to take place. For example, in a cardiac-related operation, the magnetic distortion sensors are desirably positioned in close proximity to the patient's heart to improve detection of magnetic distortions affecting the medical device therein.

In view of the present disclosure, various other configurations of a sensor for magnetic distortion detection and correction within a magnetic localization system for use during a medical procedure are readily envisioned. For example, in one embodiment, the sensor is positioned on a patient analog to replicate the positioning of a chest fixture and other leads/pads (e.g., electrocardiography ("ECG") pads, impedance-based localization system pads, among others) on a patient for an intracardiac procedure. The sensor may be generally situated on a patient's chest in proximity to the area of the patient where magnetic localization is to take place (e.g., a target area). In more specific embodiments, a plurality of sensors encircle the target area to maximize magnetic distortion detection, which can emanate from a multitude of locations within the operating room.

Specific algorithms used in conjunction with the magnetic detection sensors and processing circuitry for determining the existence of magnetic distortions within the magnetic field and the effect of the magnetic distortion on magnetic localization of the catheter within the magnetic field are presented in U.S. application Ser. No. 15/416,059, filed 26 Jan. 2017, and is hereby incorporated by reference as though fully set forth herein.

This application incorporates by reference as though fully set forth herein U.S. application Ser. No. 15/416,059, filed 26 Jan. 2017.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

What is claimed is:

1. A system to detect magnetic distortion in a magnetic field for localization of a catheter within a patient, the system comprising:
a magnetic field generator configured and arranged to generate the magnetic field for localization of the catheter within the patient; and
a magnetic detection sensor including a plurality of sensor coils, the plurality of sensor coils including:
a central coil having a first longitudinal axis, and
a plurality of peripheral sensor coils surrounding the central coil, each of the plurality of peripheral sensor coils having a longitudinal axis, wherein none of the longitudinal axes of the plurality of peripheral sensor coils intersect the first longitudinal axis of the central coil,
wherein each of the plurality of sensor coils are positioned at fixed distances and orientations relative to one another, each of the plurality of sensor coils configured and arranged to sense the magnetic field within a sensing region aligned with a longitudinal axis of the sensor coil and output an electrical signal indicative of the sensed magnetic field;
wherein the plurality of sensor coils form two substantially contiguous sensing regions, a first continuous sensing region above the magnetic detection sensor, and a second continuous sensing region below the magnetic detection sensor.

2. The system of claim 1, wherein each of the plurality of peripheral sensor coils have longitudinal axes oriented at a right angle to a longitudinal axis of an adjacent peripheral sensor coil.

3. The system of claim 2, wherein the central coil is vertically oriented.

4. The system of claim 1, wherein the plurality of peripheral sensor coils are separated from the central coil by a gap between the central coil and each of the plurality of peripheral sensor coils.

5. The system of claim 2, wherein each of the peripheral sensor coils is positioned with a longitudinal axis which is non-parallel relative to an axis of the generated magnetic field.

6. The system of claim 1, wherein the sensing regions of each sensor coil extend radially outward at an angle of approximately 30° from the longitudinal axis of the respective sensor coil.

7. The system of claim 1, wherein each of the plurality of peripheral sensor coils are oriented at an angle of 45° relative to the longitudinal axis of the central coil.

8. The system of claim 2, wherein the peripheral sensor coils are positioned substantially orthogonal relative to an axis of the generated magnetic field.

9. The system of claim 2, wherein opposing peripheral sensor coils are positioned substantially orthogonal relative to one another, and each of the peripheral sensor coils are positioned 45° relative to a horizontal plane of the magnetic field generator.

10. The system of claim 1, wherein each of the plurality of peripheral sensor coils include proximal and distal ends, wherein each of the proximal ends of the sensor coils lie in a first common plane, and each of the distal ends of the sensor coils lie in a second common plane.

11. The system of claim 10, wherein each of the plurality of sensor coils includes a center-point that lies in a third common plane.

12. The system of claim 2, wherein the peripheral sensor coils are respectively oriented 90° relative to one another about a vertical axis of the system.

13. The system of claim 1, further comprising:
processor circuitry communicatively coupled to the magnetic detection sensor, and configured and arranged to
receive electrical signals from the plurality of sensor coils indicative of an error in the calculated position of the magnetic detection sensor within the magnetic field due to magnetic distortion,
calculate a transfer function to correct for the magnetic distortion; and
compensate for the magnetic detection induced error on a calculated catheter position using the transfer function.

14. An apparatus for detecting electronic signals indicative of magnetic distortion in a magnetic field for localization of a catheter within a patient, the apparatus comprising a plurality of sensor coils including:
a central sensor coil having a longitudinal axis that is vertically orientated; and
a plurality of peripheral sensor coils circumferentially surrounding the central sensor coil and spaced from the central sensor coil such that the plurality of peripheral sensor coils are disconnected with the central sensor coil;
wherein each of the sensor coils is configured and arranged to receive energy indicative of a magnetic field strength substantially coaxial with the sensor coil, and each of the peripheral sensor coils is positioned with substantially equal perpendicularity relative to an axis of the magnetic field.

15. The apparatus of claim 14, wherein the plurality of sensor coils are configured and arranged to form two substantially contiguous sensing regions, a first continuous sensing region above the apparatus, and a second continuous sensing region below the apparatus.

16. The apparatus of claim 14, wherein each of the plurality of peripheral sensor coils have a longitudinal axis, wherein none of the longitudinal axes of the plurality of peripheral sensor coils intersect the vertically oriented longitudinal axis of the central coil.

17. The apparatus of claim 14, wherein opposing peripheral sensor coils are positioned substantially orthogonal relative to one another, and each of the peripheral sensor coils are positioned 45° relative to a horizontal plane of the apparatus.

18. The apparatus of claim 14, wherein each of the peripheral sensor coils includes proximal and distal ends, wherein each of the proximal ends of the peripheral sensor coils lies in a first common plane, and each of the distal ends of the peripheral sensors coils lies in a second common plane.

19. The apparatus of claim 18, wherein each of the plurality of sensor coils includes a center-point that lies in a third common plane.

20. The apparatus of claim 14, wherein the peripheral sensor coils are respectively oriented 90° relative to one another about a vertical axis of the apparatus.

* * * * *